United States Patent [19]

Benson et al.

[11] Patent Number: 5,524,802
[45] Date of Patent: Jun. 11, 1996

[54] POUCH FOR HOLDING MEDICAL EQUIPMENT OR PERSONAL ARTICLES

[75] Inventors: Anthony B. Benson, Arlington; Kevin K. Brunson, Argyle, both of Tex.

[73] Assignee: Tecnol Medical Products, Inc., Fort Worth, Tex.

[21] Appl. No.: 325,821

[22] Filed: Oct. 19, 1994

Related U.S. Application Data

[63] Continuation-in-part of Ser. No. 127,781, Sep. 27, 1993, Pat. No. 5,392,973.

[51] Int. Cl.$^6$ ............................................. A45F 5/02
[52] U.S. Cl. .................. 224/194; 224/269; 224/603; 224/660
[58] Field of Search ............................ 224/194, 252, 224/269, 253, 901, 902, 224, 228, 236, 237, 904; 24/3 R, 3 J, 3 L, 32 R; 383/22, 31, 71

[56] References Cited

U.S. PATENT DOCUMENTS

| D. 358,475 | 5/1995 | Choksi et al. | D3/203 |
|---|---|---|---|
| 882,178 | 3/1908 | Sloat | 224/904 |
| 1,188,955 | 6/1916 | Leonard . | |
| 1,779,207 | 10/1930 | Candar . | |
| 2,295,143 | 9/1942 | Watkins | 224/902 |
| 2,618,086 | 11/1952 | Komorous | 24/3 L |
| 2,897,865 | 8/1959 | Jackman | 383/31 |
| 3,361,312 | 1/1968 | Hutchison | 224/252 |
| 3,469,768 | 9/1969 | Repko | 229/56 |
| 4,037,633 | 7/1977 | Gordon | 383/31 |
| 4,069,955 | 1/1978 | Noyes | 224/5 H |
| 4,088,136 | 5/1978 | Hasslinger et al. | 128/349 |
| 4,315,641 | 2/1982 | Larsen | 280/822 |
| 4,347,956 | 9/1982 | Berger | 224/202 |
| 4,411,267 | 10/1983 | Heyman | 128/385 |
| 4,416,315 | 11/1983 | Foley | 224/252 |
| 4,420,078 | 12/1983 | Belt et al. | 224/253 |
| 4,637,535 | 1/1987 | Aleman | 224/202 |
| 4,674,664 | 6/1987 | Simon | 224/215 |
| 4,793,486 | 12/1988 | Konopka et al. | 206/438 |
| 4,872,599 | 10/1989 | Hubbard et al. | 224/208 |
| 5,116,306 | 5/1992 | Zander | 602/19 |
| 5,121,864 | 6/1992 | Geschwind | 224/230 |
| 5,244,136 | 9/1993 | Collaso | 224/237 |
| 5,255,833 | 10/1993 | McAllister | 224/236 |
| 5,392,973 | 2/1995 | Benson | 224/236 |

FOREIGN PATENT DOCUMENTS

| 996517 | 9/1976 | Canada | 224/6 |
|---|---|---|---|
| 1013424 | 7/1977 | Canada . | |
| 1162169 | 2/1984 | Canada | 224/1 |
| 18310 | 1/1907 | United Kingdom . | |
| 476706 | 12/1937 | United Kingdom | 224/32 R |

OTHER PUBLICATIONS

Journal of the American Medical Association, vol. 168, No. 7, p. 930, Oct. 18, 1958.

*Primary Examiner*—Henry J. Recla
*Assistant Examiner*—Gregory M. Vidovich
*Attorney, Agent, or Firm*—Baker & Botts

[57] ABSTRACT

A pouch (12) is provided for maintaining a medical unit, such as a telemetry unit (14), adjacent a patient (10) or personal articles or communication equipment on a person in a clean room environment. The pouch (12) includes a transparent front wall (34) and a non-woven material back wall (36) which are attached along a portion (38) of the periphery of the walls (34, 36). The transparent front wall (34) allows the telemetry unit (14) or personal articles to be viewed during use. The pouch (12) additionally includes a flap (42) with a reactivating, resealable adhesive strip (46) for releasably covering the top opening (41) of the pouch (12). The pouch (12) may be secured to the patient (10) or wearer by straps (18, 20) or a clip (52).

3 Claims, 2 Drawing Sheets

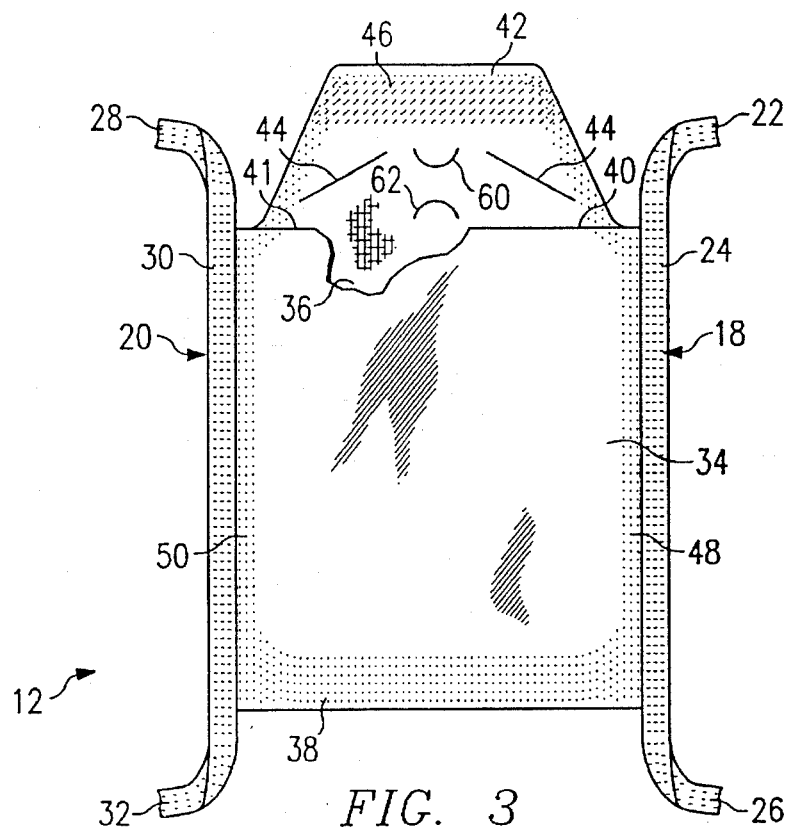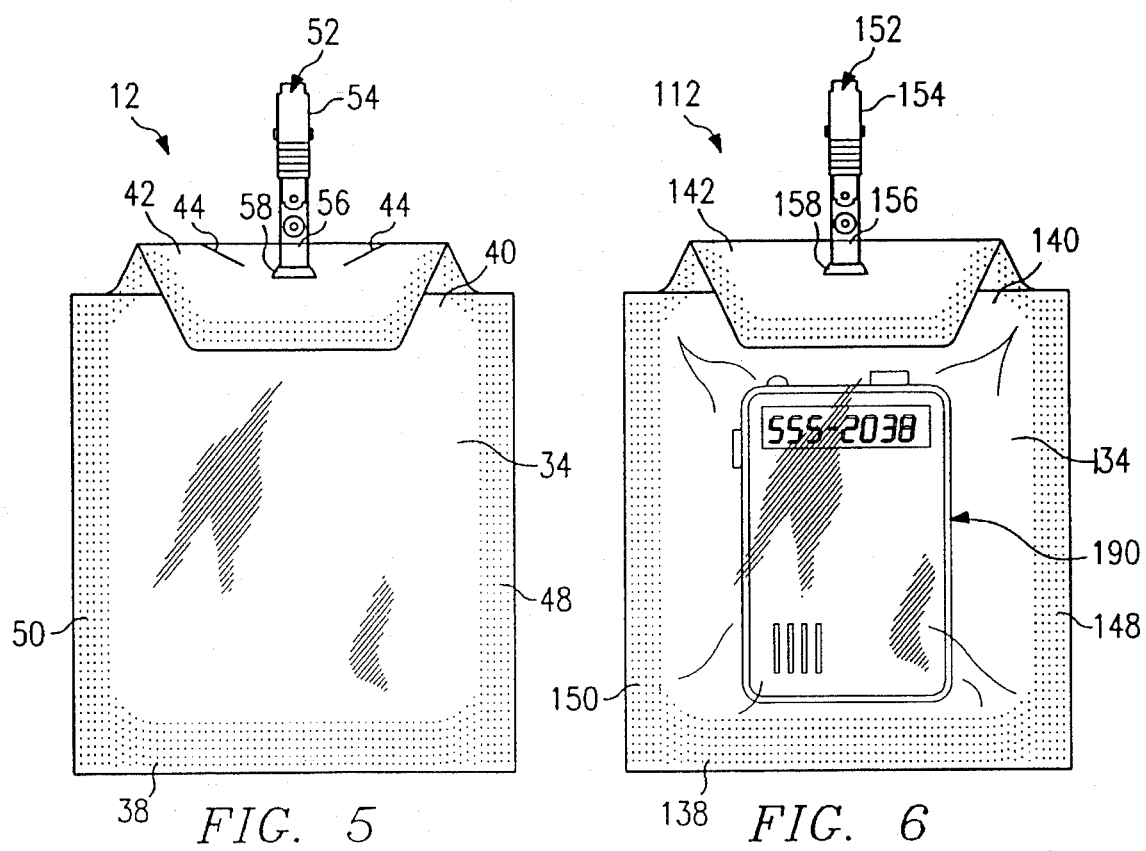

POUCH FOR HOLDING MEDICAL EQUIPMENT OR PERSONAL ARTICLES

RELATED APPLICATIONS

This application is a continuation in part of co-assigned application Ser. No. 08/127,781, filed Sep. 27, 1993, which is now U.S. Pat. No. 5,392,973 dated Feb. 28, 1995 and entitled *Telemetry Pouch*.

TECHNICAL FIELD OF THE INVENTION

The present invention relates to medical and clean room apparatus, and more particularly to a pouch-like apparatus for removably securing items to a patient or person.

BACKGROUND OF THE INVENTION

Telemetry monitoring has become widely used in the care of patients such as coronary patients. Many hospitals now have sophisticated equipment to continuously monitor the condition of a coronary patient by portable individual telemetry units and a centralized receiving and recording system.

Several types of telemetry pouches have been developed to attach a telemetry unit to a patient. One type of telemetry pouch provides two layers of an opaque polyolefin material secured about their periphery to form a pocket. This first type of telemetry pouch does not allow the telemetry equipment to be viewed without removal of the unit from the pouch. Additionally, the open top of the pouch allows moisture and contaminants to invade the pocket.

A second type of telemetry pouch provides a rigid foam, such as styrofoam, pouch with a small window cut in the front face of the pouch to allow viewing of a specified portion of a telemetry unit for which the pouch was designed. This pouch has some shortcomings. First, the rigid foam may be hot and uncomfortable to the patient. Second, the pertinent part of the telemetry unit may only be viewed when the specific type of telemetry unit for which the pouch was designed is used with the pouch.

Another type of telemetry pouch is formed of cloth material sewn at the edges and provided with straps to tie the pouch around the patient's neck. This type of pouch is not designed to prevent moisture from coming in contact with the pouch nor to allow viewing of the telemetry pouch during use.

Another type of telemetry pouch is formed of two non-breathable plastic sheets secured together to form a pocket with sealable top. This type of pouch resembles and functions like a ZIPLOC® brand freezer bag. Since this type of pouch does not allow air to permeate the bag and cool the telemetry unit, the pouch may become quite hot and uncomfortable for the patient to wear.

One example of prior telemetry pouches is shown in U.S. Pat. No. 4,872,599 entitled *Telemetry Pouch* with *Expansible Chest Strip* to Vance M. Hubbard and Welton K. Brunson. U.S. Pat. No. 4,872,599 is incorporated by reference for all purposes in this application.

In some manufacturing and assembly environments requiring clean rooms, such as semiconductor processing, it has on occasion been inconvenient to find a place to store small and/or personal items. Further, in a clean room environment, it may be desirable to be able to view the contents of a holder for personal articles without requiring that the holder be opened. Also, workers in clean room environments may use communication equipment and telemetry equipment depending upon the type of process being performed in the clean room.

SUMMARY OF THE INVENTION

The present invention provides a pouch for use in medical or clean room applications that eliminates or substantially reduces the shortcomings of the prior art pouches. According to one aspect of the present invention, a pouch for holding medical equipment, such as a telemetry unit, adjacent to a patient is provided. The pouch may be formed with a clear front wall. The clear front wall allows the front of all medical equipment used with the pouch to be viewed. The pouch provides a flap having a reactivating, resealable adhesive strip for releasably securing the flap over the top opening of the pouch.

According to another aspect of the present invention, a pouch is provided having a clear front wall and a clip that allows for convenient storage and viewing of communication equipment and/or small, personal items in a clean room environment. In accordance with another aspect of the present invention, a telemetry pouch is provided which can receive various types of telemetry units and allow full viewing of any telemetry unit contained within the pouch. The telemetry pouch is formed from selected materials which keep the telemetry unit dry and may allow air to permeate the pouch and cool the telemetry unit. These materials result in a pouch which is cooler for a patient to wear for extended periods of time. The pouch is also constructed from materials in an economical manner to allow the pouch to be disposable.

BRIEF DESCRIPTION OF THE DRAWINGS

A more complete understanding of the invention and its advantages will be apparent from the detailed description taken in conjunction with the accompanying drawings in which:

FIG. 3 is an elevational view with portions broken away showing a central portion of the telemetry pouch of FIGS. 1 and 2;

FIG. 5 is an elevational view of the telemetry pouch shown in FIG. 4; and

FIG. 6 shows an elevational view of a pouch adapted for use in a clean room environment according to an aspect of the present invention.

DETAILED DESCRIPTION OF THE INVENTION

The preferred embodiments of the present invention and its advantages are best understood by referring to FIGS. 1–6 of the drawings, like numerals being used for like and corresponding parts of the various drawings. In the description below, any of various types of telemetry units 14 are described as fitting in pouch 12, but it is to be understood that other medical equipment may be used with pouch 12, and telemetry unit 14 is described as just one example.

Figure 1:
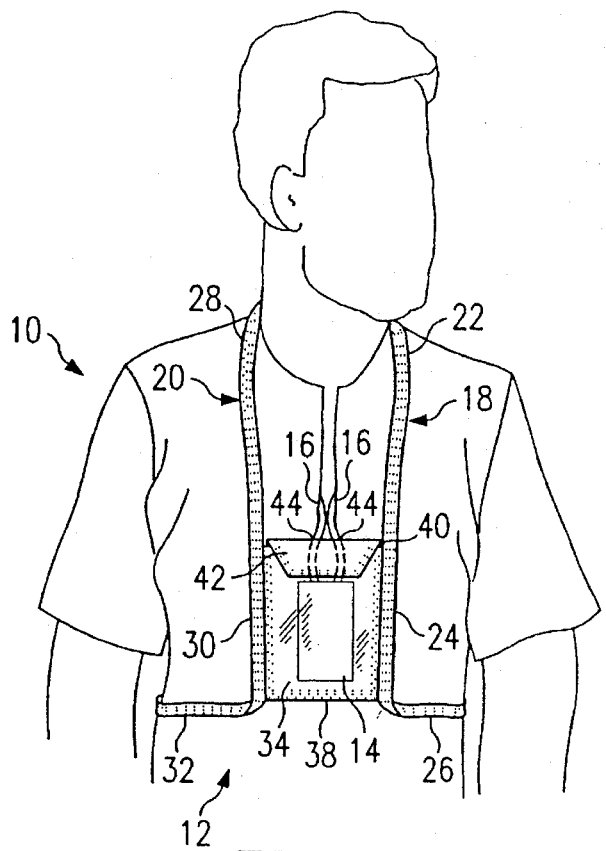
FIG. 1 is a schematic view of a first embodiment of the telemetry pouch of the present invention shown attached to the patient in a front position.
Figure 2:
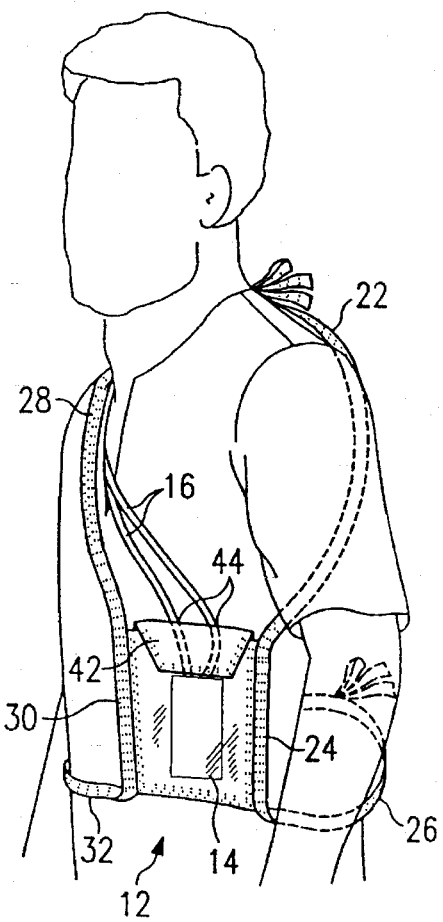
FIG. 2 is a schematic view of the telemetry pouch of FIG. 1 shown attached to the patient in a side position.

Referring to FIG. 1, patient 10 is fitted with pouch 12 in a front position. Telemetry unit 14, may be connected to the patient by cables 16. Pouch 12 is secured to patient 10 by first strap 18 and second strap 20. First strap 18 has a first portion 22, a second portion 24 and a third portion 26. Likewise, second strap 20 has a first portion 28, a second portion 30 and a third portion 32. First portion 22 of first strap 18 and first portion 28 of second strap 20 may be tied behind the neck of patient 10. Third portion 26 of first strap 18 and third portion 32 of second strap 20 may be tied behind the back of patient 10. See FIG. 2. Pouch 12 may be positioned in a front position (FIG. 1) or a side position (FIG. 2). In this fashion, first strap 18 and second strap 20 provides securing means for securing pouch 12 to patient 10.

Telemetry unit 14 is held or maintained adjacent to patient 10 by pouch 12. When in position, telemetry unit 14 is visible through a front wall 34 of pouch 12. Front wall 34, preferably formed from transparent material, for example, a blown polypropylene, is attached to a back wall 36. Back wall 36 may be formed from any light weight material such as polyolefin, polypropylene, hydro-entangled polyester or spun bond/melt blown/spun bond (SMS), etc. In the preferred embodiment, the material of back wall 36 is a non-woven material in the form of a spun bonded polyolefin such as TYVEK®, which is available from DuPont.

Front wall 34 and back wall 36 are attached along a first portion 38 of their periphery, but a second portion 40 is not attached. Second portion 40 defines a top opening 41 for receiving telemetry unit 14. Back wall 36 may have a flap extension 42 coupled to back wall 36. Flap extension 42 is formed to fold and cover top opening 41. Flap extension 42 contains at least one cable opening 44 for allowing cables 16 to pass to monitoring sites (not shown) on patient 10.

Referring to FIG. 3, there is shown a schematic view of a central portion of pouch 12 shown in FIGS. 1 and 2. Flap extension 42 is shown in an open position; in this position, reactivating, resealable adhesive strip 46 is visible. Adhesive strip 46 allows flap extension 42 to be releasably secured to transparent front wall 34 once telemetry unit 14 is placed within the pocket formed by front wall 34 and back wall 36. Reactivating, resealable adhesive strip 46 may be, for example, fastener tape available from the 3M Company (Product No. 9920). Adhesive strip 46 may include other adhesive closing devices.

Cable openings 44 may be formed as slots in flap extension 42. Cable openings 44 may be omitted if the application does not call for these openings such as may be the case for personal article holders for use in clean rooms. Front wall 34 and back wall 36 may be ultrasonically bonded along first portion of periphery 38 of walls 34 and 36. A second portion of periphery 40 defines top opening 41 of pouch 12. Once a pocket is formed by front wall 34 and back wall 36, various types of securing means may be attached to allow the pouch to be secured to patient 10.

One securing means is straps 18 and 20. Second portion 24 of first strap 18 may be ultrasonically bonded or bonded by other means known in the art such as bonding by heat and pressure or by stitching with thread to first edge 48 of the periphery of front wall 34 and back wall 36. Strap portion 24 may be folded about its length to encase walls 34 and 36 along edge 48 and then attached by means known in the art such as thermal bonding or ultrasonic bonding. Likewise, second portion 30 of second strap 20 may be attached by means known in the art such as ultrasonically bonding to second edge 50 of the periphery formed by front wall 34 and back wall 36. Strap portion 30 may be folded about its length to encase walls 34 and 36 along edge 50 and then attached.

Figure 4:
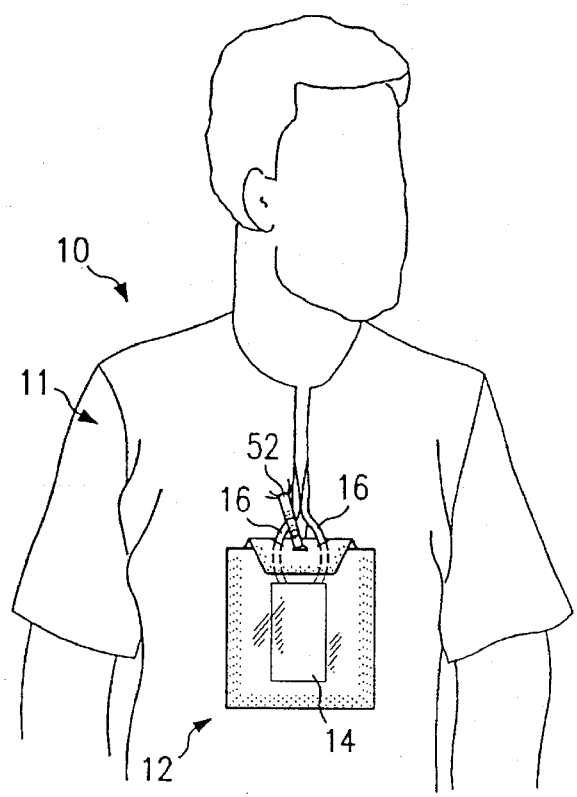
FIG. 4 is a schematic view of a second embodiment of the telemetry pouch of the present invention shown attached to the patient in the front position.

An alternative embodiment of pouch 12 showing an alternative securing means is shown in FIGS. 4–6. Referring to FIG. 4, pouch 12 is shown secured to garment 11 of patient 10. Referring to FIG. 5, clip 52 is shown secured to pouch 12. Clip 52 may have alligator jaws 54 for gripping garment 11 and loop 56 for securing pouch 12 to clip 52. Loop 56 of clip 52 is passed through clip opening 58. Clip opening 58 may be formed by a first clip opening 60 and a second clip opening 62 on flap extension 42 as shown in FIG. 3. In other respects, the embodiment shown in FIGS. 4 and 5 is substantially the same as the embodiment shown in FIGS. 1 through 3. Slots 44 may be omitted if the end application does not require them, such as may be the case for personal article holders for use in clean rooms. One example of personal articles holder or pouch 112 for use in clean rooms is shown in FIG. 6. The pouch 112 for use in clean rooms is identical to pouch 12 of FIG. 5, with the exception that slots 44 have been removed and pouch 112 is shown with a communication device, beeper 190, in pouch 112. Other parts corresponding to the previously shown embodiments are referenced by adding 100 to the previously mentioned reference numerals of the earlier embodiments.

In manufacturing pouch 12, the manufacturer may provide a transparent front wall 34 such as a clear plastic film, and a back wall 36. The manufacturer may then attach a first portion 38 of the periphery of walls 34 and 36 to form a pocket for receiving telemetry unit 14 or personal articles. The manufacturer may couple to back wall 36 or form as an integral part thereof, flap extension 42. A reactivating, resealable adhesive strip 46 may be applied to flap extension 42 and cable openings 44 are created. If the securing means is to be clip 52, first and second clip openings 60 and 62 are formed in flap 42. First and second clip openings 60 and 62 may be semicircular openings to distribute forces along a greater length. A securing means may then be attached to front wall 34 and back wall 36.

If the securing means is clip 52, loop 56 may be passed through opening 58 formed by first and second clip openings 60 and 62. If the securing means is to be straps 18 and 20, second portion 24 of first strap 18 is then attached to first edge 48 of the periphery of walls 34 and 36. Second portion 30 of second strap 20 may then be attached to second edge 50 of the periphery of walls 34 and 36. Portions 24 and 30 may be secured by any means known in the art, but in the preferred embodiment are ultrasonically bonded. With this latter securing means, the first portions of straps 18 and 20 may then be tied behind the neck of patient 10, and the third portions of straps 18 and 20 may be tied about the waist or torso of patient 10. Straps 18 and 20 may be formed of a non-woven material. To strengthen straps 18 and 20, each strap may be folded lengthwise, the second portion 24 or 30 may be aligned to encase first or second edge 48 or 50 of portion 38 of the periphery of walls 34 and 36. Alternatively, each strap may be folded over on itself and ultrasonically bonded about its length before being attached to edge or portions 38 and 40.

To use pouch 12 with a telemetry unit, telemetry unit 14 is inserted through top opening 41 into pouch 12. Cables 16 are then passed through cable openings 44, and flap extension 42 may be folded over towards front wall 34 and adhesive 46 may engage front wall 34. Transparent front wall 34 allows telemetry unit 14 to be viewed during use in pouch 12. Back wall 36, which is made of a relatively cool backing material is placed against patient 10. Pouch 12 is then secured to patient 10 by a securing means. If the embodiment of FIGS. 1 through 3 is used, straps 18 and 20 are tied around patient 10 as previously described. If the embodiment of FIGS. 4 and 5 is used, pouch 12 is secured with clip 52. If pouch 12, is to be used to hold personal articles in a clean room, instead of inserting telemetry unit 14, the personal articles may be placed in pouch 12 for some applications, small items or communication equipment, e.g., personal pager 190, may be placed in pouch 12 for view by and communication with personnel working in a clean room.

Although the present invention and its advantages have been described in detail, it should be understood that various changes, substitutions and alterations can be made therein without departing from the spirit and scope of the invention as defined by the appended claims.

What is claimed is:

1. A pouch for holding personal articles to a person's clothes in a clean room environment, the pouch comprising:
   a transparent front wall;
   a back wall, the back wall attached to the front wall along a first portion of the periphery of the front and back walls and a second portion of the periphery forming a top opening for receiving the personal articles;
   a flap extension coupled to the back wall proximate the top opening, the flap extension having front and back surfaces and a first clip opening and a second clip opening each extending through the front and back surfaces of the flap extension;
   an adhesive reactivating, resealable strip provided on the flap extension for releasably attaching the flap extension to the front wall;
   a releasable clip for releasably securing the pouch to the person, the releasable clip comprising:
      a loop portion for passing through the first and second clip openings to thereby secure the clip to the flap extension, and
      an alligator jaws portion coupled to the loop for releasably attaching to the person's clothes;
   wherein the flap extension coupled to the back wall has an open position defined when the adhesive, reactivating, resealable strip is unattached from the front wall and a closed position defined when the reactivating, resealable adhesive strip is attached to the front wall; and
   wherein the first clip opening and the second clip opening are spaced so that the first clip opening and second clip opening are approximately aligned when the flap extension is in the closed position.

2. A method of manufacturing a pouch for holding a medical unit adjacent to a patient, the steps comprising:
   providing a transparent front wall;
   providing a back wall formed of a non-woven material;
   ultrasonically bonding the transparent front wall and the back wall along a portion of their periphery to form a pocket therebetween, the pocket having a top opening for receiving the medical unit;
   providing a flap extension on the back wall for folding over the top opening;
   forming a cable opening in the flap extension for passing cables from monitoring sites to the medical unit;
   attaching a reactivating, resealable adhesive strip on the flap extension for releasably securing the flap extension to the transparent front wall;
   forming a clip opening in the flap extension; and
   attaching a clip having a loop portion and an alligator jaws portion to the flap extension by securing the loop through the clip opening of the flap extension.

3. A method of manufacturing a pouch for use in holding personal articles adjacent to a person in a clean room environment, the steps comprising:
   providing a transparent front wall;
   providing a back wall formed of a non-woven material;
   bonding the transparent front wall to the back wall to form a pocket therebetween, the pocket having a top opening;
   providing a flap extension on the back wall for folding over the top opening, the flap extension having front and back surfaces;
   attaching a reactivating, resealable adhesive strip on a portion of a periphery of the flap extension for releasably securing the flap extension to the transparent front wall;
   forming a clip opening extending through the front and back surfaces of the flap extension; and
   attaching a clip in the clip opening for releasably securing the pouch to the person.

* * * * *